(12) United States Patent
Coleman et al.

(10) Patent No.: US 7,360,543 B1
(45) Date of Patent: Apr. 22, 2008

(54) PATIENT ASSIST LIFT

(75) Inventors: Gary Coleman, Dallas, TX (US); Michael Wilson, Winnsboro, TX (US)

(73) Assignee: Itec Manufacturing, Ltd, Winnsboro, TX (US)

( * ) Notice: Subject to any disclaimer, the term of this patent is extended or adjusted under 35 U.S.C. 154(b) by 65 days.

(21) Appl. No.: 11/353,292

(22) Filed: Feb. 10, 2006

(51) Int. Cl.
*A61B 19/00* (2006.01)
*A61F 5/37* (2006.01)
*A47B 1/00* (2006.01)

(52) U.S. Cl. ............ 128/870; 128/877; 128/869; 5/628

(58) Field of Classification Search ............ 128/870, 128/877, 869; 5/625, 628, 637
See application file for complete search history.

(56) References Cited

U.S. PATENT DOCUMENTS

| | | | | |
|---|---|---|---|---|
| 4,422,454 A | * | 12/1983 | English | 128/870 |
| 4,528,981 A | * | 7/1985 | Behar | 5/637 |
| 4,627,428 A | | 12/1986 | Brooks | |
| 4,794,656 A | * | 1/1989 | Henley, Jr. | 5/628 |
| 5,014,374 A | * | 5/1991 | Williams | 5/628 |
| 5,016,620 A | * | 5/1991 | Matthews | 602/19 |
| 5,921,945 A | * | 7/1999 | Gray | 602/5 |
| 6,122,778 A | | 9/2000 | Cohen | |
| 6,659,104 B2 | * | 12/2003 | Kiefer et al. | 128/870 |
| 6,991,612 B2 | * | 1/2006 | Scheinberg et al. | 602/6 |
| 2004/0187214 A1 | * | 9/2004 | Holland | 5/626 |
| 2005/0241068 A1 | * | 11/2005 | Tomcany et al. | 5/622 |

FOREIGN PATENT DOCUMENTS

WO    WO92/10155    6/1992

OTHER PUBLICATIONS mediccom.org/public/tadmat/training/NDMS/Litter_evac_1.pdf.

* cited by examiner

*Primary Examiner*—Justine R. Yu
*Assistant Examiner*—K C Matter
(74) *Attorney, Agent, or Firm*—David W. Carstens; Carstens & Cahoon, LLP (57) ABSTRACT

A patient assist lift (PAL) device comprising a contoured shell which provides many benefits to patients and rescuers. A PAL device reduces or eliminates the risks of injuring a patient during mobilization. A PAL device may be quickly and easily attached to a patient, and supports hips, spine, torso, and neck. Color coded straps encourage proper use of a PAL device. Ergonomic handles and straps reduce or eliminate injury to rescuers during lifting and movement of an injured person. A PAL device enables rescuers to lift and mobilize an injured person from any position and in any situation. A PAL device is especially effective in emergencies in providing a safe and efficient means to secure and move a patient with the least amount of effort while minimizing the risks and discomfort to both patient and rescuer in mobilizing such patient. A smaller PAL device can be used to immobilize children or extremities.

12 Claims, 7 Drawing Sheets

PATIENT ASSIST LIFT

BACKGROUND

1. Technical Field

The present invention relates generally to a means of immobilizing and moving an injured person (patient). A patient often requires the assistance of one or more rescue workers to move him or her to a place of safety where he or she may receive further attention. Such patient may suffer additional injury if moved improperly. Carrying a patient by his or her arm or clothing would be inappropriate because such means are neither designed nor adapted for easy grasping. Further, because of the difficulty of grasping a patient who needs to be moved, a caregiver or rescue worker may also sustain injuries such as a sprained back or pulled muscles. Injuries to caregivers and rescue workers are particularly likely when it is necessary to quickly move a patient due to emergency circumstances.

2. Description of Related Art

Certain patents and publications have disclosed concepts associated with securing or moving injured persons, but none meet the needs filled by the present invention. For example, U.S. Pat. No. 6,122,778 issued Sep. 26, 2000 to Cohen describes a lift vest or garment-like device which enables caregivers to assist a patient in moving from one position to another. Such vest is distinguishable from the present invention because it is meant to be attached to only the upper torso of a patient and does not provide sufficient immobilization to reduce the potential of further injury to the patient. Further, such vest is not designed to be used in emergency situations where the time to secure a patient may be minimal.

U.S. Pat. No. 4,627,428 issued Dec. 9, 1986 to Brooks discloses a child safety restraint for a medical transporting device. The apparatus includes a semi-rigid base and a cover or harness which holds a patient between the base and the cover. The lower layer of material has apertures through which fastening members of the semi-rigid support extend. This invention is further distinguishable as it is used only in conjunction with patient stretchers and ambulances.

Finally, a Kendricks extraction device (KED) and spine boards have been used for many years on patients with suspected spinal injuries. The present invention is distinguishable from such devices in that it is designed to be used in all types of rescue situations. Further, a KED is a short board and is principally used for sitting patients. KED boards do not have specially designed handles and straps for the convenience and benefit of rescuers.

None of these inventions solves the problem of safely and efficiently immobilizing essentially any patient in any type of rescue situation and allowing the patient to be moved without the threat of increased potential injury to both the patient and the rescuer. Consequently, a need exists for a device to assist rescuers in immobilizing and moving all varieties of persons suspected of having an injury. Also, a need exists for a device which enables rescuers to lift or move a person from any position. Also, a need exists for a device which reduces or eliminates the risks of further injuring a person during such immobilization and movement. Also, a need exists for a device which may be quickly and easily attached to an injured person, providing support for the hips, spine, torso, and neck of the person. And finally, a need exists for a device which reduces the risk of injury to rescuers during lifting and transporting an injured person. The present invention fills these needs and others as detailed more fully below.

SUMMARY OF THE INVENTION

A patient assist lift (PAL) is a contoured, flexible immobilization and transport device which provides many benefits to injured persons and rescuers in a variety of situations. A PAL reduces or eliminates the risk of additional injury to a patient during immobilization and transport and may be quickly and easily attached to an injured person by utilizing nylon straps. Once properly attached around a patient, the nylon straps cause the PAL to conform to the patient, providing support to the patient's hips, spine, torso, and neck. A smaller version of a PAL may also be used to immobilize and support an injured child, infant, or even an isolated extremity.

A PAL provides additional benefits to rescuers in that it is lightweight, thin, buoyant, durable, and simple to use. Ergonomic handles attached to the nylon straps provide a means to reduce or eliminate injury to rescuers during lifting and movement of an injured person. Color coded straps also encourage proper and efficient use of the PAL by providing visual indication to determine if the straps have been properly fastened around a patient. Once fastened, a PAL enables rescuers to immobilize and lift the patient from virtually any position. Being lightweight and thin allows maximum portability and ease of handling in rescue situations. The buoyancy of a PAL also provides an additional margin of safety and support when performing a water rescue. Finally, it is possible to trim material from a PAL in order to provide a custom fit for very unique rescue situations.

The invention accordingly comprises the features described more fully below, and the scope of the invention will be indicated in the claims. The objects of the present invention will become apparent in the following detailed description.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

REFERENCE NUMERALS

102 patient assist lift (PAL)
104 handle
106 strap
108 buckle
112 length of PAL
114 width of PAL
116 narrow end of PAL
118 hip-supporting portion
202 patient
304 automobile seat
402 cervical restraint
404 soft cylinders
406 cylinder connecting material
502 head strap
504 chin strap
510 cervical collar
508 head of patient
602 water
702 transportation backboard
704 backboard slot
802 limb brace strap
804 buckle
806 strap retention slot
808 limb brace
810 limb
812 injury site
814 extremity
822 nylon strap with hook and loop fastener
824 foot securing strap
826 tensioning strap

DETAILED DESCRIPTION

While the invention is described below with respect to a preferred embodiment, other embodiments are possible. The concepts disclosed herein apply equally to other devices for supporting and facilitating the transportation of an injured person or patient. The invention is described below with reference to the accompanying figures.

Figure 1:
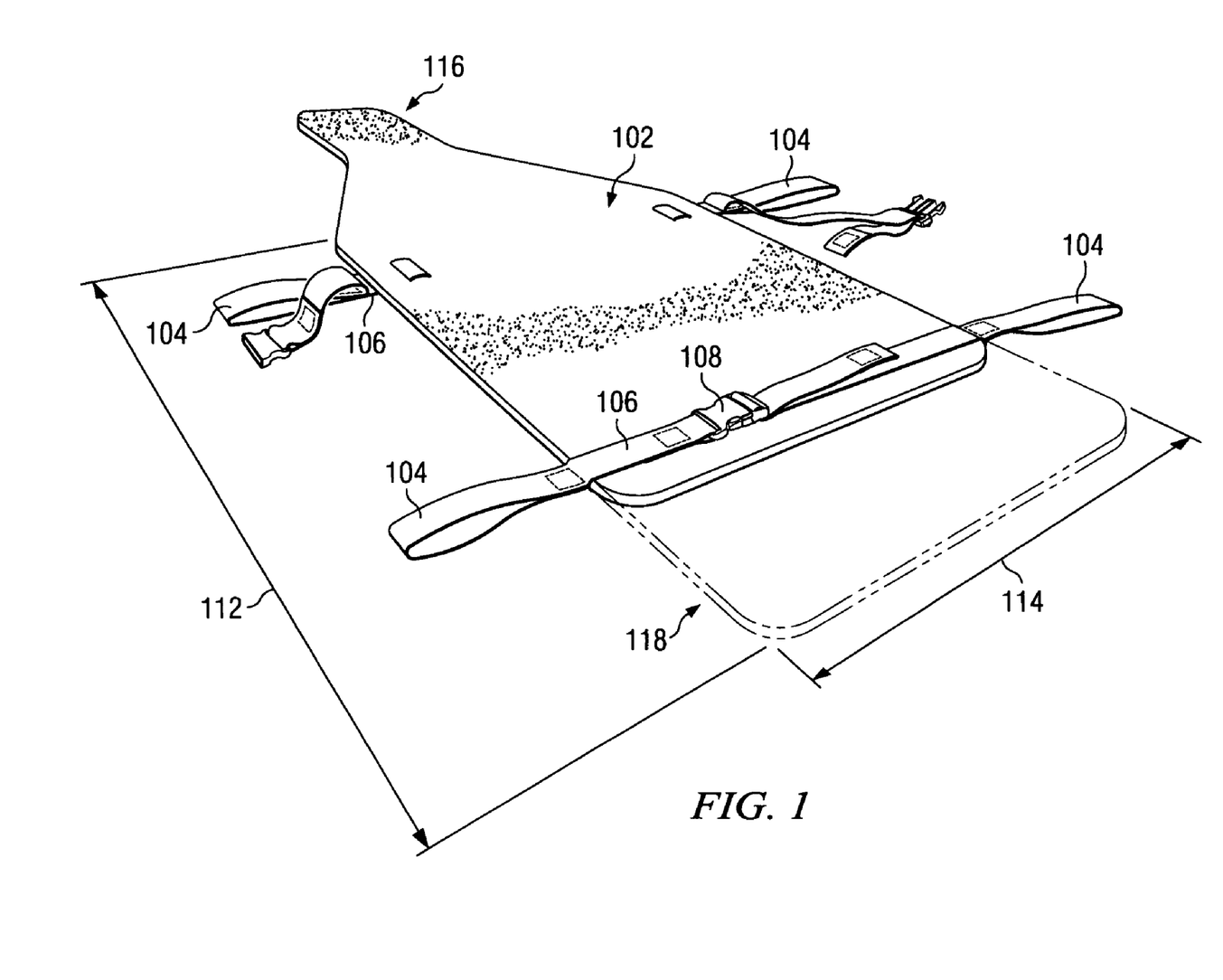
FIG. 1 is a perspective view of the preferred embodiment of the present invention showing a patient assist lift device.

FIG. 1 shows a perspective view of a patient assist lift (PAL) 102 according to a preferred embodiment of the invention. The overall shape of the PAL 102 is roughly that of the silhouette of a human torso. The overall length 112 and width 114 can be varied such that the PAL 102 can ultimately conform to any sized human torso; from a very large adult to the smallest of infants. The length 112 can be further varied to provide a hip supporting portion 118 for the hips of a patient. Depending upon the rescue situation, hip support 118 may or may not be practical. Thus, the PAL 102 can be sized appropriately for any rescue situation and for any sized patient.

This embodiment shows two straps 106 attached to the PAL 102, each strap 106 being essentially one piece with attached handles 104. Also, each strap 106 is attached to the flexible shell of the PAL 102 using slots cut in the shell material. Each strap 106 also wraps around the outside of the PAL 102 to provide additional support when conforming the shell to a patient. As shown, the straps 106 utilize single adjustable side release buckles 108 that serve to allow the PAL 102 to be attached around a patient and properly tensioned. Another potential method of fastening the straps 106 around a patient would be with hook and loop fasteners. Thus, any means of fastening the straps 106 would be sufficient so long as the means allows for proper tensioning of the straps 106 around the patient.

The shell of the PAL 102 can be constructed of any flexible material that can conform to a patient. In the preferred embodiment, the shell is constructed of ¹⁄₁₆ inch HDPE (high density polyethylene) plastic. This material serves to make the PAL 102 lightweight and conformable while providing a tough outer surface that provides an extra measure of protection to a patient. This durable material protects a patient against bruises and scrapes that could occur during movement over rough terrain or other sharp obstacles. In addition, because this material is waterproof and lighter than water, it adds buoyancy to the PAL 102 in water rescue situations. Further yet, the surface friction of HDPE is reduced when wet and thus the outer shell of the PAL 102 becomes easier to slide over rough surfaces such as might be present in a water rescue in which the rescuer pulled the patient with attached PAL 102 onto the bank over rocks or other objects.

In addition, the PAL 102 can be lined on the inside surface ("patient" side) with ½ inch closed cell polyethylene foam material. In this configuration, the buoyancy, cushioning, and protective properties of the PAL 102 are greatly increased. The foam material is waterproof and lighter than water, and can literally allow the PAL 102 to float a moderately sized patient during a water rescue situation. Also, the cushioning properties of this foam material in conjunction with an HDPE outer support shell afford increased protection from impacts that could potentially occur during movement over rough terrain or other sharp obstacles. Another benefit of using this type of foam material for an inner lining is that it better protects the delicate skin of certain patients with advanced diseases that render the skin susceptible to injury with even the slightest touch.

Still another benefit of an embodiment of the PAL 102 that utilizes either an HDPE outer shell or an HDPE outer shell in conjunction with a closed cell polyethylene foam inner liner is that it is relatively inexpensive and thus disposable. In a rescue situation a PAL 102 would likely be subjected to significant abuse that would render further uses impractical. For instance, an injured patient would likely be losing bodily fluids which could contaminate the surfaces of the PAL 102. Although waterproof in this embodiment, decontamination might possibly be less cost-effective than mere disposal and replacement of the PAL 102.

Figure 2:
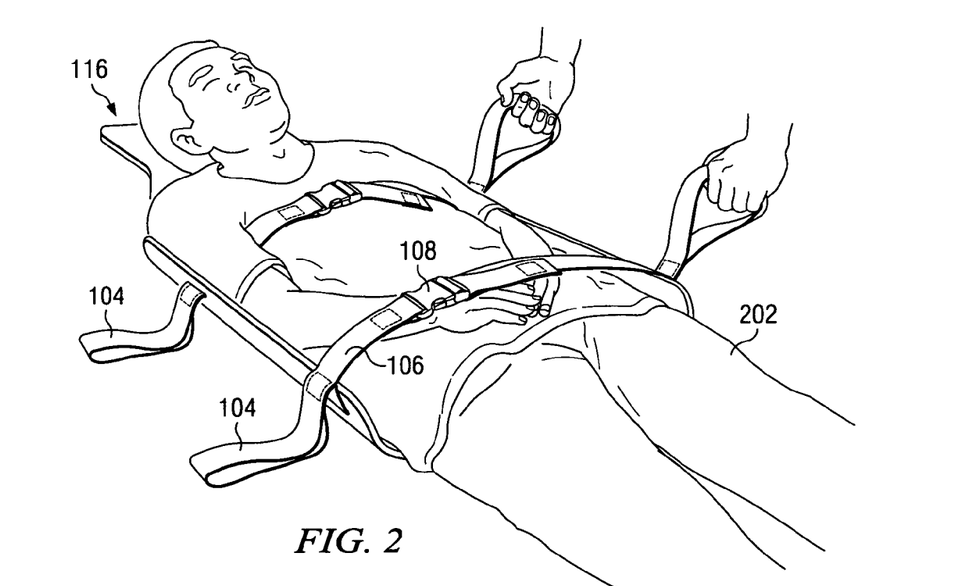
FIG. 2 is a perspective view of the preferred embodiment of the present invention showing a patient secured to a patient assist lift device.

FIG. 2 shows the preferred embodiment being utilized to immobilize and move a patient 202. With respect to FIG. 1, straps 106 with buckles 108 allow the device to conform to the patient 202 and thus immobilize the patient. The PAL 102 in this embodiment is made of a ¹⁄₁₆ inch HDPE flexible support shell. The flexibility of the support shell is what allows the PAL 102 to conform. Once the straps 106 are correctly fastened around the patient 202, the straps 106 can be tightened sufficiently to draw the sides of the PAL 102 snugly around the patient 202. Extra tensioning of the straps 106 further helps to secure and encapsulate the patient 202 within the PAL 102 and does not put undue pressure on the patient 202. Once conformed to the patient 202, the PAL 102 becomes a circular truss that resists bending and thus acts as an upper torso "splint" that supports the patient's spine and prevents unnecessary movement which, if allowed, would likely further aggravate injuries.

Handles 104 in the preferred embodiment provide an efficient and effective means for a rescuer to lift and move the patient 202. These handles 104 afford a comfortable and safe means of grasping and lifting the patient 202 using a PAL 102 in its preferred embodiment. A rescuer lifting the patient 202 is better able to use a correct lifting technique and thus minimize the possibility of either mishandling the patient or else causing injury to his or her own body.

Figure 3:
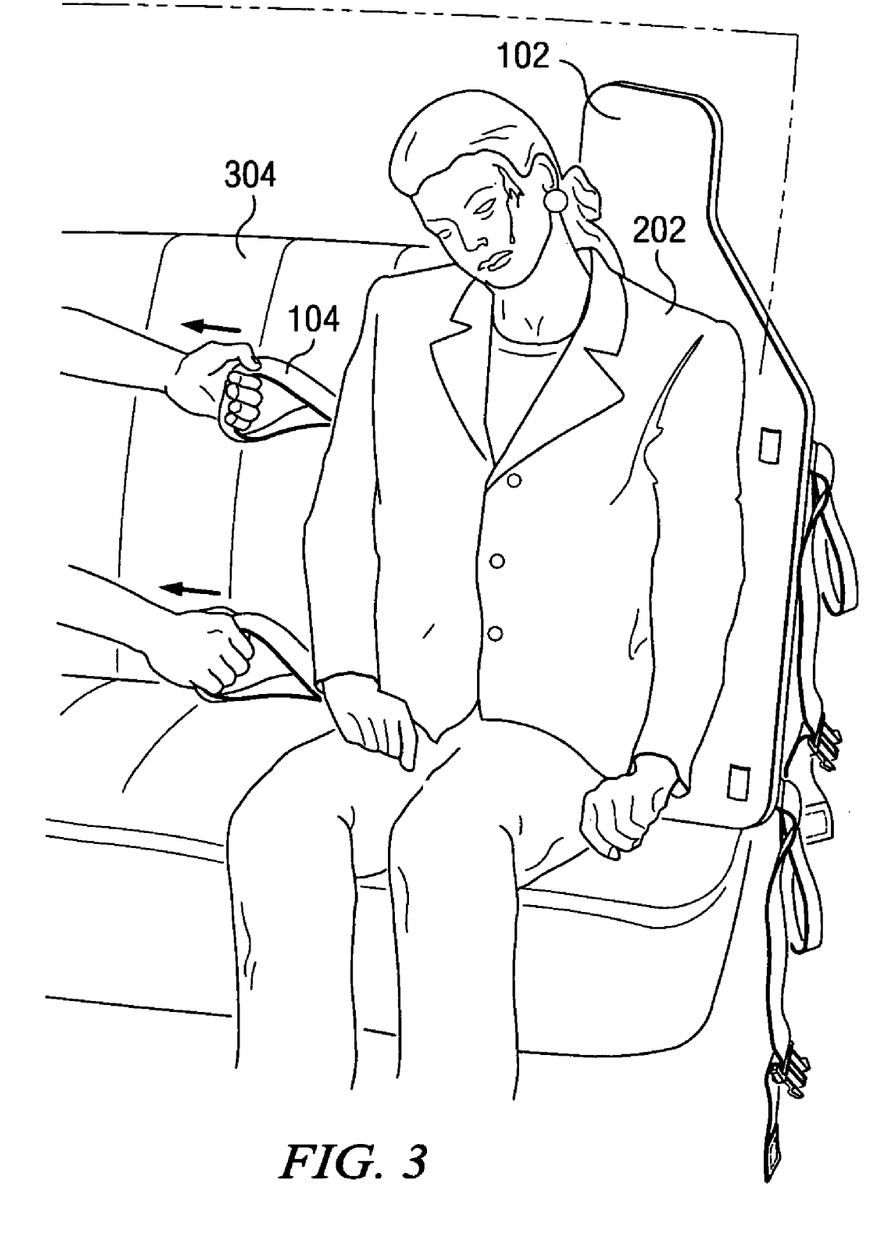
FIG. 3 is a perspective view of the preferred embodiment of the present invention being utilized to extract an injured person from an automobile seat.

FIG. 3 shows the use of a PAL 102 in its preferred embodiment in an automobile crash rescue situation. In this situation, and with respect to FIG. 1, a PAL 102 without the extra hip-supporting portion 118 is most effective. Because the PAL 102 is both thin and lightweight, it can be easily slid between the injured patient and the car seat 304 by pulling on the handles 104 as shown. Once in place, the PAL 102 can be attached to the patient 202 using the straps 106 and drawn snugly around the patient's torso. Once the PAL 102 is secured to the patient 202, the patient can be more easily extricated by grasping the handles 104 and gently pulling the patient 202 from the car seat 304. The correctly attached PAL 102 serves to maintain proper torso alignment of the patient 202 and thus prevents additional injury due to unnecessary movement.

Figure 6:
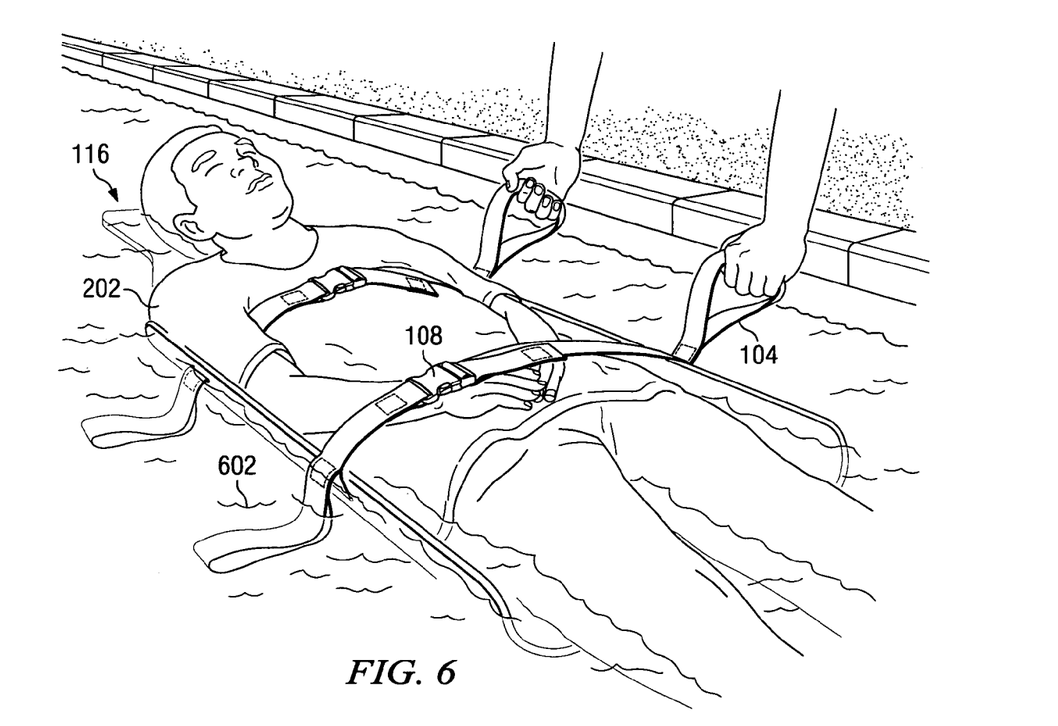
FIG. 6 is a perspective view of the preferred embodiment of the present invention showing a patient secured to a patient assist lift device being rescued from water.

FIG. 6 shows the use of a PAL 102 in its preferred embodiment in a water rescue situation. With respect to FIG. 1, The PAL 102 in this embodiment is made of a 1/16 inch HDPE flexible backing with a 1/2 inch closed cell polyethylene foam interior surface. The use of a flexible plastic support shell coupled with the closed cell foam provides additional buoyancy when the PAL 102 is properly attached to the patient 202 in water 602. This additional buoyancy reduces stress on the patient 202 by allowing the patient 202 to float more easily. Thus, the risk of the patient 202 submerging and drowning is greatly reduced. This added buoyancy also assists rescuers in extracting the patient 202 from the water 602 because of the additional "lift" it generates to compensate for the weight of the patient 202. The plastic support shell in this embodiment provides support for the patient's 202 torso and hips and protects the patient 202 from scrapes and other injuries which could occur, for instance, if the patient 202 should happen to strike a submerged object. Also, the plastic support shell in this embodiment provides a low friction surface that allows a rescuer to more easily slide the patient 202 from the water. For example, a rescuer extracting the patient 202 with an attached PAL 102 from a swimming pool can grasp the handles 104 and slide the patient over the pool edge and onto the pool deck more easily due to the low friction provided by the plastic support shell. The plastic support shell and closed cell foam interior surface in this embodiment would also protect the patient 202 from scrapes and further injury due to the sliding action.

Figure 4:
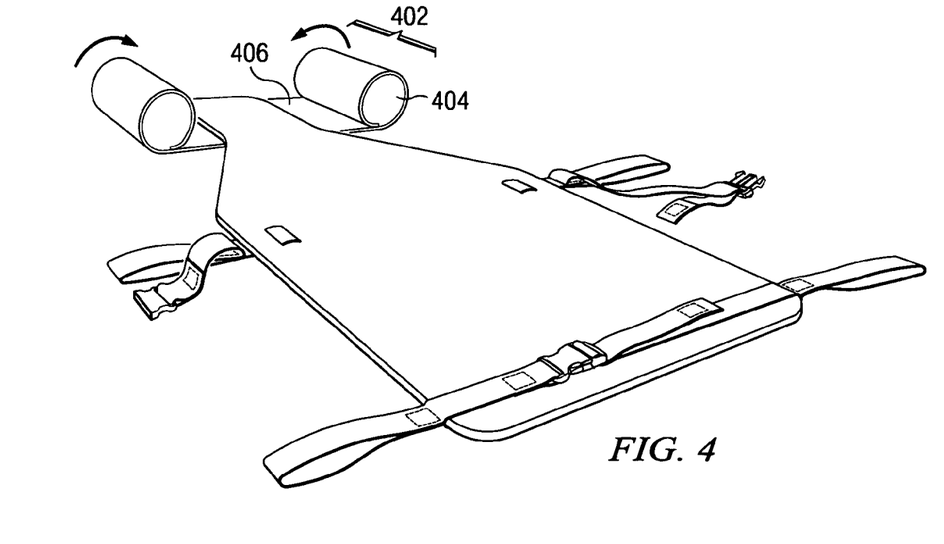
FIG. 4 is a perspective view of the preferred embodiment of the present invention showing a patient assist lift device with a cervical restraint.
Figure 5:
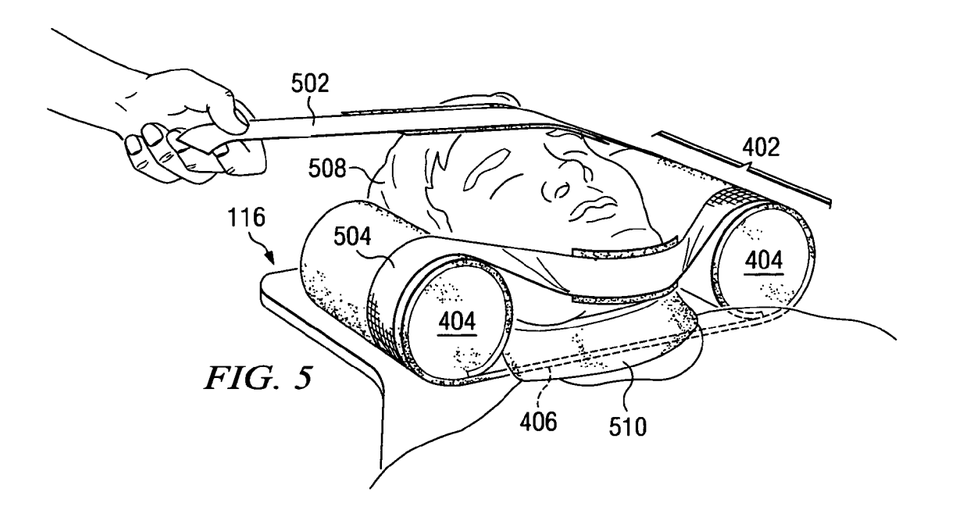
FIG. 5 is a perspective view of an embodiment of the present invention showing a cervical restraint used in conjunction with a cervical collar to immobilize the head and neck of a patient.

FIGS. 4 and 5 provide a perspective view of another embodiment of a patient assist lift (PAL) 102 with a cervical restraint 402. The cervical restraint 402 in this embodiment is comprised of two soft foam cylinders 404 connected together by a flexible foam material 406 such as that used to line the interior surface of the PAL 102. When properly utilized, the cervical restraint 402 cradles a patient's head (see FIG. 5). In a water rescue situation, the cervical restraint 402 provides additional buoyancy to the patient 202, allowing the patient's 202 head to float even higher in the water. Also, the soft foam materials used to construct the cervical restraint 402 provide cushioning and stability for the patient's 202 head and neck.

Figure 7:
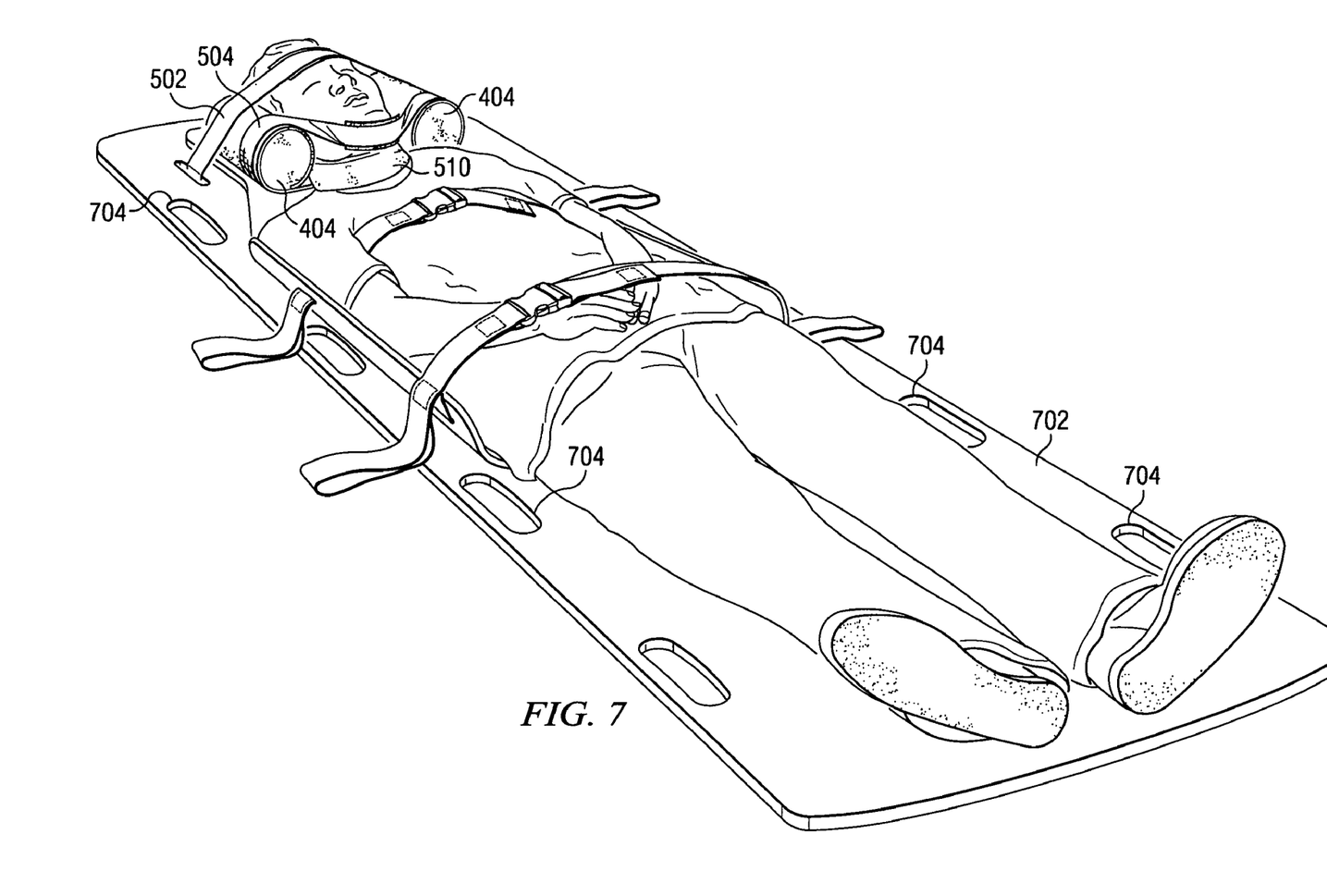
FIG. 7 is a perspective view of an embodiment of the present invention showing a patient secured to a patient assist lift device, with a cervical restraint and cervical collar being used to immobilize the head and neck, and lying on a transportation backboard.

FIG. 5 is a close-up perspective view of this embodiment of a PAL 102 utilizing a cervical restraint 402 to immobilize a patient's head and neck. The patient 508 in this figure also utilizes a cervical collar 510 for additional immobilization support. As this embodiment shows, the two soft foam cylinders 404 are rolled apart and the flexible foam material 406 used to connect the two cylinders 404 is placed beneath the patient's 508 head. In this position, the cervical restraint 402 cradles the patient's head and provides cushioning support. This embodiment also shows two straps (one head strap 502 and one chin strap 504) used to attach the cervical restraint 402 to the patient 508. The head strap 502 wraps around the patient's 508 head to hold the cylinders 404 snugly against the patient's 508 head. The head strap 502 then wraps beneath the narrow end 116 of the PAL 102 to further immobilize the patient. FIG. 7 is a perspective view further showing the patient 508 immobilized by the present embodiment utilizing a cervical restraint 402 with the optional cervical collar 510 and lying on a backboard 702. The patient's 508 head is immobilized by the cervical restraint 402 as indicated above. The head strap 502 is passed around the outside of the backboard 702 for attachment beneath. Once attached, this effectively immobilizes patient's 508 head, neck, and spine for easy transport by a rescuer who lifts the backboard 702 using the provided slots 704 as hand grips.

Figure 8A:
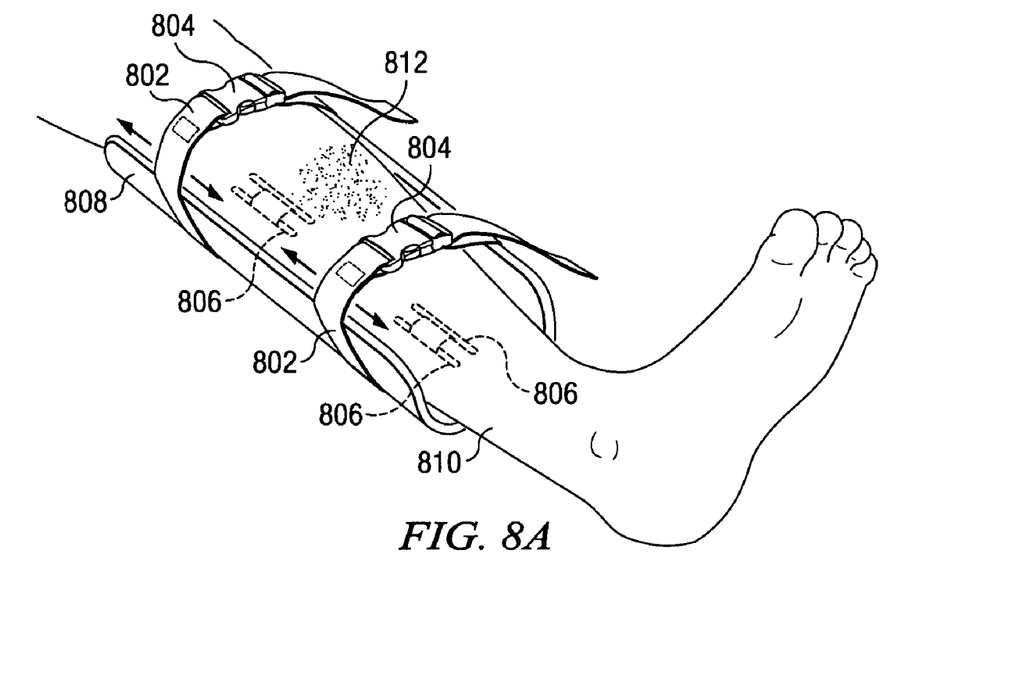
FIG. 8A is a perspective view of an embodiment of the present invention showing it secured to a patient's injured leg in a splint fashion by means of nylon straps utilizing adjustable buckles.

FIG. 8A is a perspective view of another embodiment of the present invention showing a patient's leg 810 secured to a limb brace 808 acting as a splint device. With reference to FIG. 1, the limb brace 808 is made of the same or similar materials, and according to the same principles, as those used to make a PAL 102 device of FIG. 1. The limb brace 808 is secured by at least two straps 802. The ends of the straps are connected by buckles 804. A limb brace 808 may be made with any number of straps to properly secure and accommodate a patient's limb 810. A limb brace 808 may likewise be of any length or width to accommodate varying lengths and sizes of limbs 810 and for applying a limb brace 808 to part or all of a limb 810. Preferably, at least one strap 802 is placed above an injury site 812, and at least one strap 802 is placed below such injury site 812. Slots 806 in the limb brace 808 allow for positioning of the straps 802 along the length of the limb brace 808 and away from any injury site 812. Such positioning may be made for patient comfort or for proper immobilization of a patient's limb 810.

Figure 8B:
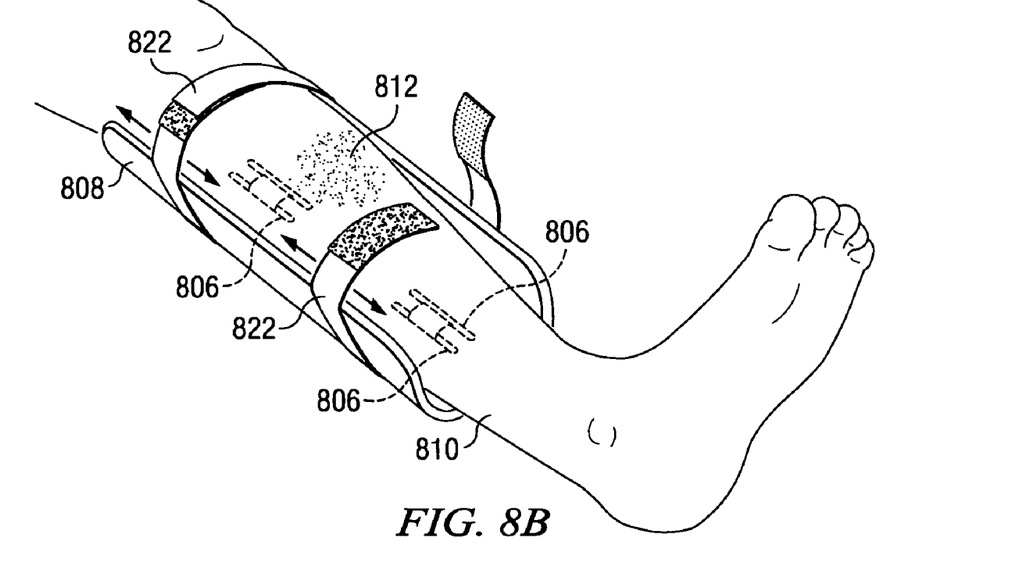
FIG. 8B is a perspective view of an embodiment of the present invention showing it secured to a patient's injured leg in a splint fashion by means of nylon straps utilizing hook and loop fasteners; and, FIG. 8C is a perspective view of an embodiment of the present invention showing it secured to a patient's injured leg and foot in a splint fashion by means of nylon straps utilizing buckles.

FIG. 8B is a perspective view of a limb brace 808 as shown in FIG. 8A wherein the straps 802 are secured by hook and loop fasteners 822 instead of buckles 804. With reference to FIG. 8B, hook and loop fasteners 822 may provide increased comfort and better fit of the limb brace 808 to the patient's limb 810. Also, with reference to FIG. 8B, the limb brace 808 is made of the same or similar materials, and according to the same principles, as those used to make a PAL 102 device as shown in FIG. 1.

Figure 8C:
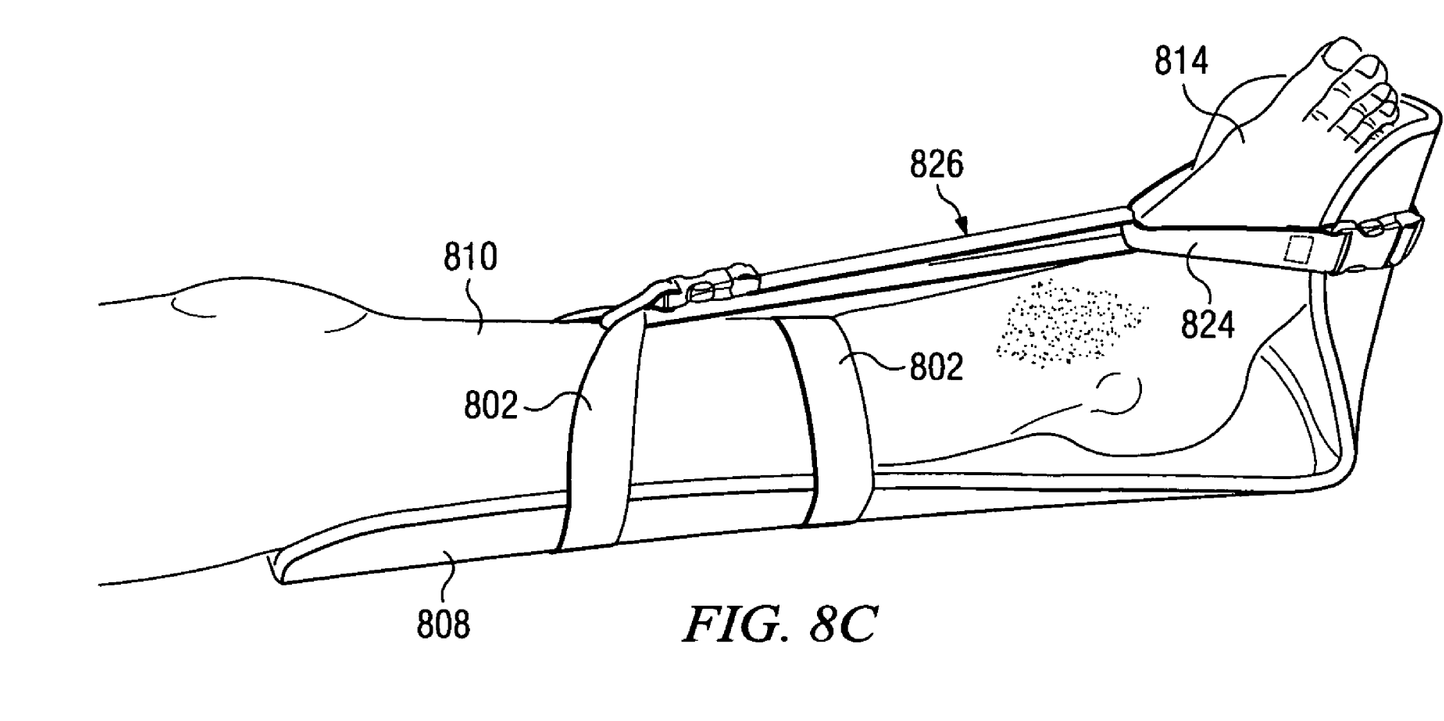

FIG. 8C shows a perspective view of another use of the limb brace 808 as shown in FIGS. 8A and 8B. With reference to FIG. 8C, a patient's leg 810 and foot 814 are secured to a limb brace 808. In this embodiment, the angle of repose of the patient's extremity 814 is fixed by a foot-securing strap 824. This foot-securing strap 824 passes through slots 806 in the limb brace 808 near the patient's foot 814 and is secured at the opposite end of the limb brace 808 to at least one other strap 802 by a tensioning strap 826. The limb brace 808 may be contoured to the patient's foot 814 by cutting one or more short slots (not shown) into the limb brace 808 at or near the bend in the limb brace 808. Such cuts are from the side of the limb brace 808 toward its center. Such cuts may be made at any angle relative to the side of the limb brace 808. A limb brace 808 is preferably made of materials which may by easily cut or adapted to a limb and which still provide sufficient support for its intended purposes. A limb brace 808 may be used on any extremity or portion of an extremity, and such limb brace 808 may be adapted to any contour as appropriate to the situation. For example, a limb brace 808 may be fit to a wrist and hand, or to a bent knee.

The foregoing discussion of the invention has been presented for purposes of illustration and description. Further, the description is not intended to limit the invention to the form disclosed herein. Consequently, variation and modification commensurate with the above teachings, within the skill and knowledge of the relevant art, are within the scope of the present invention. The embodiments described herein are further intended to explain the best mode presently known of practicing the invention and to enable others skilled in the art to use the invention. It is intended that the appended claims be construed to include alternate embodiments to the extent permitted.

We claim:

1. A patient assist lift device for treating a patient suffering from trauma to the head, neck, or torso, the patient assist lift comprising:
   a cervical restraint, the cervical restraint comprising:
      a strip, wherein the strip is thin, flexible, and constructed of closed cell foam, the strip for placement behind the patient's head;
      two polystyrene foam cylinders, wherein the cylinders are attached to opposing ends of the strip, and wherein the cylinders have a natural tendency to roll inwards on the strip and towards the center of the strip;
      a chin strap, wherein the chin strap supports the patient's chin and secures the lowermost portion of the two foam cylinders to the sides of the patient's head; and
      a head strap, wherein the head strap secures the patient's forehead between the two foam cylinders and the upper most portion of the two foam cylinders is secured to the sides of the patient's head;
   a flexible plastic support shell, the support shell having an interior surface and an exterior surface, the interior surface for accepting a patient; and
   a plurality of straps, wherein the straps releasably fasten the shell to the patient and cause the shell to generally conform to the patient, and wherein the straps are affixed to the exterior surface of the shell.

2. A patient assist lift as in claim 1 further comprising at least one handle attached to at least one of said straps.

3. A patient assist lift as in claim 1 further comprising a closed cell foam sheet attached to said interior surface of said support shell.

4. A patient assist lift as in claim 1 further comprising a closed cell foam sheet attached to the interior surface of the support shell and wherein the patient assist lift is buoyant.

5. A patient assist lift as in claim 1 further comprising a closed cell foam sheet attached to the interior surface of the support shell and wherein the foam sheet is approximately ½ inch thickness closed cell polyethylene foam.

6. A patient assist lift as in claim 1 wherein said support shell is approximately 1/16 inch thickness HDPE.

7. A patient assist lift as in claim 1 wherein said patient assist lift is disposable.

8. A patient assist lift as in claim 1 wherein at least one of the straps includes a fastener chosen from the group consisting of an adjustable side release buckle and a hook and loop fastener.

9. A patient assist lift as in claim 1 wherein at least one of said straps is fixedly retained by at least one slot in said support shell.

10. A patient assist lift as in claim 1 wherein at least one of said straps is slidably retained by at least one elongated slot in said support shell.

11. A patient assist lift as in claim 1 wherein said plastic support shell is shaped in the form of a human torso silhouette and is sized to fit a torso chosen from the group consisting of an adult, a child, and an infant.

12. The method for immobilizing and moving an injured, seated patient from a vehicle or other confined space using a patient assist lift as embodied in claim 1, the method comprising:
   (a) selecting the properly sized patient assist lift for the patient;
   (b) sliding the patient assist lift into proper position behind the patient;
   (c) securing the patient assist lift's upper strap across the chest of the patient and directly beneath the patient's armpits;
   (d) securing the patient assist lift's lower strap across the hips of the patient;
   (e) tightening the upper and the lower straps alternately and firmly so as to cause the patient assist lift to wrap around and approximately conform to the patient;
   (f) installing the cervical restraint on the patient comprising the steps of:
      separating the two foam cylinders by rolling them outwards;
      positioning the centerline of the strip between the patient's head and the patient assist lift, the foam cylinders on either side of the patient's head;
      rolling the foam cylinders inward against the patient's head;
      placing the chinstrap over the patient's chin and wrapping the ends around the outer side of the cylinders and the strip;
      attaching the chinstrap ends such that the ends of the foam cylinders closest to the patient's chin are pulled snugly against the sides of the patient's head;
      wrapping the head strap over the patient's forehead and around the foam cylinders; and
      attaching the head strap behind the patient assist lift such that the foam cylinders are pulled snugly against the sides of the patient's head and the patient's head is held firmly against the patient assist lift;
   (g) turning the patient's back towards the extraction point using the handles attached to the patient assist lift; and
   (h) removing the patient from the vehicle or other confined space using the handles.

* * * * *